(12) United States Patent
Falter et al.

(10) Patent No.: US 8,596,127 B2
(45) Date of Patent: Dec. 3, 2013

(54) METHOD FOR THE NON-DESTRUCTIVE TESTING OF OBJECTS USING ULTRASOUND

(75) Inventors: Stephan Falter, Simmerath (DE);
Roman Koch, Blankenbach (DE);
Walter De Odorico, Kelkheim (DE);
Gerhard Finger, Limeshain (DE);
Klaus-Peter Busch, Rodenbach (DE)

(73) Assignee: GE Inspection Technologies, Huerth (DE)

( * ) Notice: Subject to any disclaimer, the term of this patent is extended or adjusted under 35 U.S.C. 154(b) by 364 days.

(21) Appl. No.: 12/994,471

(22) PCT Filed: May 28, 2009

(86) PCT No.: PCT/EP2009/056581
§ 371 (c)(1),
(2), (4) Date: Feb. 7, 2011

(87) PCT Pub. No.: WO2009/150066
PCT Pub. Date: Dec. 17, 2009

(65) Prior Publication Data
US 2011/0132091 A1 Jun. 9, 2011

(30) Foreign Application Priority Data

May 28, 2008 (DE) .......................... 10 2008 002 860

(51) Int. Cl.
*G01N 29/44* (2006.01)
(52) U.S. Cl.
USPC ................................. 73/627; 73/598; 73/602
(58) Field of Classification Search
USPC ............. 73/627, 609, 610, 624–26, 628, 633,
73/641, 597, 598, 602; 600/443, 447
See application file for complete search history.

(56) References Cited

U.S. PATENT DOCUMENTS

| 4,180,790 | A | | 12/1979 | Thomas |
| 4,241,610 | A | | 12/1980 | Anderson |
| 4,528,854 | A | | 7/1985 | Shimazaki |
| 5,014,712 | A | | 5/1991 | O'Donnell |
| 5,235,982 | A | | 8/1993 | O'Donnell |
| 5,357,962 | A | * | 10/1994 | Green .......................... 600/443 |
| 5,846,201 | A | | 12/1998 | Adams |
| 5,851,187 | A | | 12/1998 | Thomas et al. |
| 6,315,723 | B1 | * | 11/2001 | Robinson et al. ............. 600/443 |
| 6,789,427 | B2 | * | 9/2004 | Batzinger et al. ............... 73/614 |
| 6,792,808 | B1 | * | 9/2004 | Batzinger et al. ............... 73/602 |
| 7,841,982 | B2 | * | 11/2010 | Johnson et al. .............. 600/437 |
| 7,874,988 | B2 | * | 1/2011 | Shiki ............................ 600/443 |
| 7,987,724 | B2 | * | 8/2011 | Takada ............................ 73/641 |
| 8,246,543 | B2 | * | 8/2012 | Johnson et al. .............. 600/442 |
| 2010/0242613 | A1 | * | 9/2010 | Simard et al. ................... 73/641 |

* cited by examiner

*Primary Examiner* — J M Saint Surin
(74) *Attorney, Agent, or Firm* — Global Patent Operation; Mark A. Conklin

(57) ABSTRACT

The invention relates to a method for processing signals which are generated by the reflection of ultrasonic waves by defects in the surface of objects during the non-destructive testing of objects such as pipes, bars, sheet metal, or uniform and complex carbon-fiber components. Said method comprises the following steps: emission of a complete wavefront onto at least one test section of the object, using a plurality of independent emission elements; receiving a wave reflected by the structure of the object by means of a plurality of receiver elements that are independent of one another; digitalization of the signals received by the receiver elements in digitizing steps; continuous modification of delay values and/or the number of receiver elements for each digitalization step (on-the-fly).

20 Claims, 10 Drawing Sheets

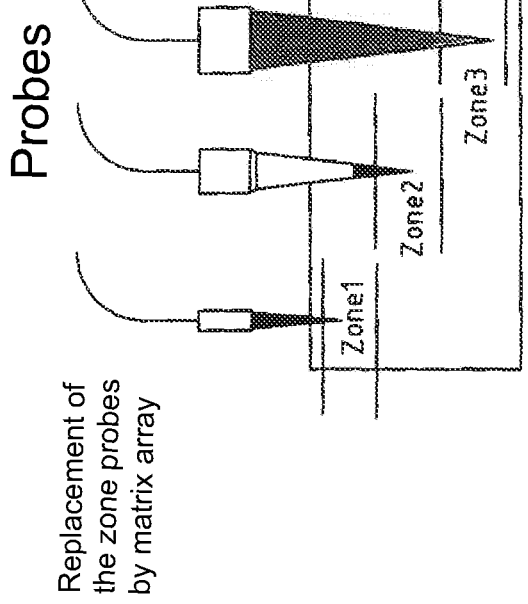
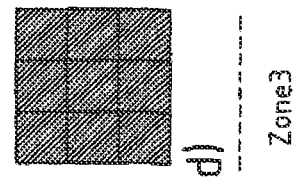
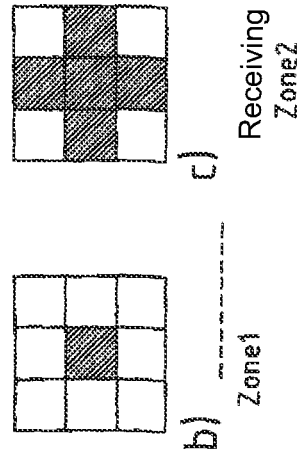
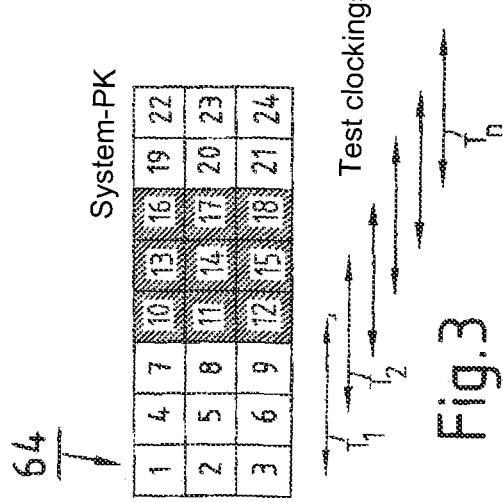
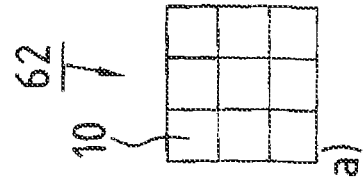

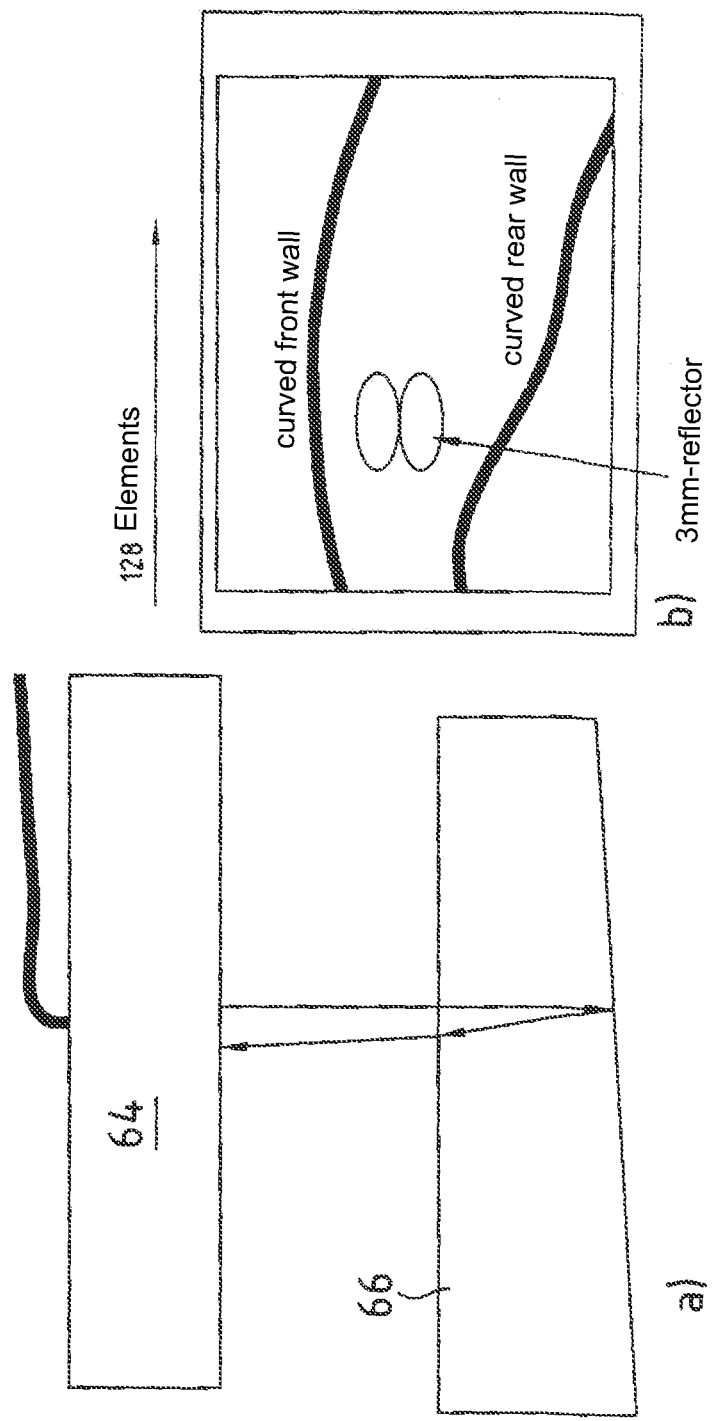

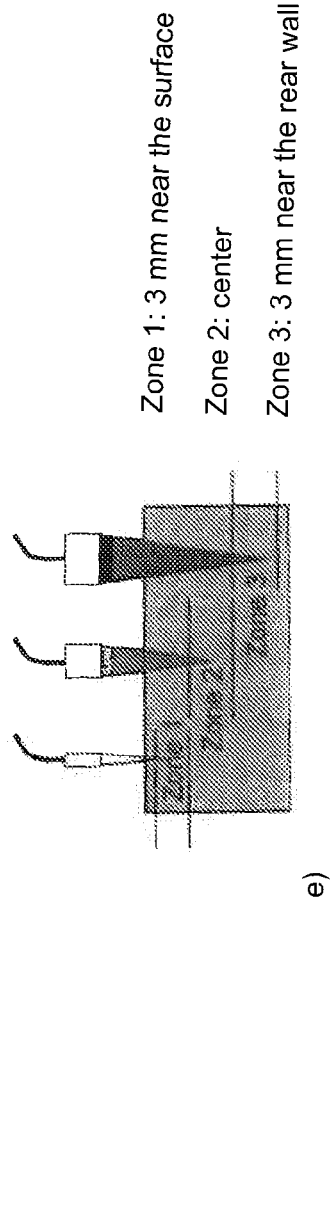
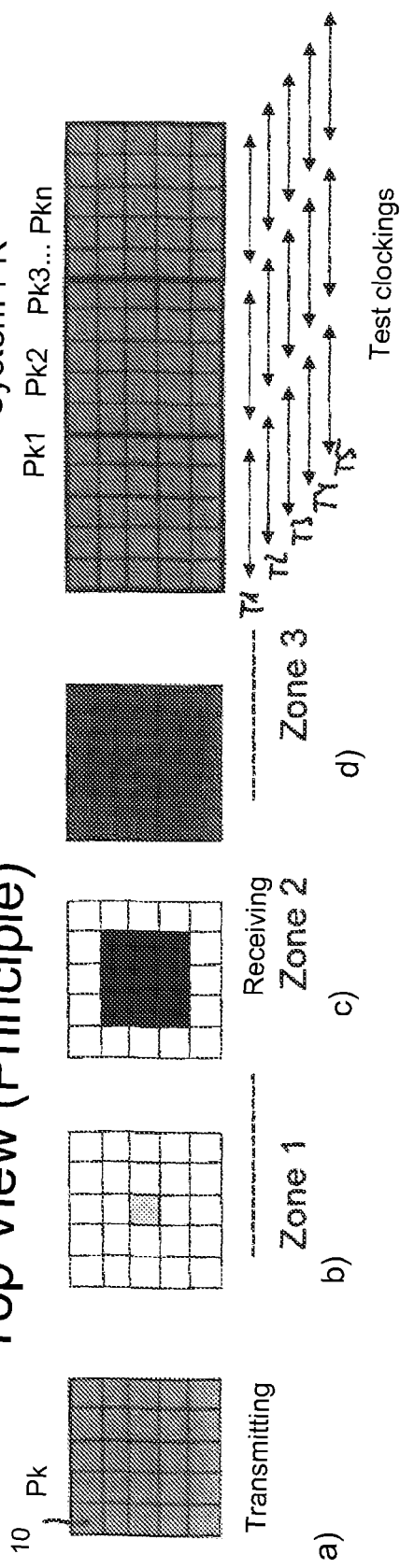
Fig. 7
Fig. 8

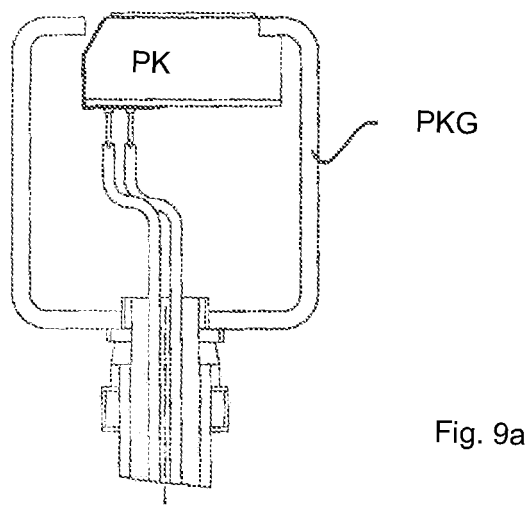
Fig. 9a
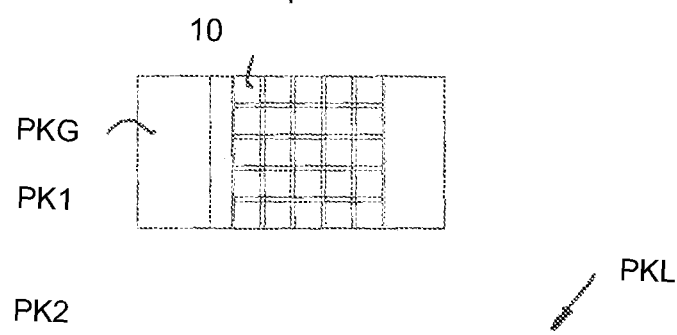
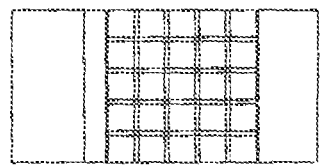
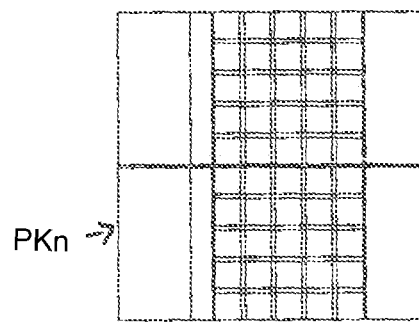
Fig. 9b

METHOD FOR THE NON-DESTRUCTIVE TESTING OF OBJECTS USING ULTRASOUND

BACKGROUND OF THE INVENTION

The invention relates to a method for processing signals, which are generated by the reflection of ultrasonic waves by defects in the surface of objects during the non-destructive testing of objects such as pipes, bars, sheet metal, or uniform and complex carbon-fiber components.

A method of the type mentioned at the outset is described in DE-A-10 2005 051 781, which relates to a method for the non-destructive inspection of a test piece using ultrasound. In the case of this method, ultrasound waves are coupled with one or a plurality of ultrasound transducers into the test piece and ultrasound waves reflected inside the test piece are received by a plurality of ultrasound transducers and converted into ultrasound signals. An ultrasound transducer is provided and activated on a surface of the test piece, such that the ultrasound waves coupled to the test piece are propagated spatially and distributed largely uniformly within the test piece. Subsequently, the ultrasound waves reflected within the test piece are received by a plurality m of ultrasound transducers provided on the surface and m ultrasound time signals are generated, in which time-resolved amplitude information is contained.

The m ultrasound time signals are saved. Subsequently, a 3-dimensional volume-image, a sector image in the form of a 2-dimensional ultrasound image through the test piece or an A-image in the form of a 1 dimensional time and location resolving ultrasound signal along a presettable intromission angle, is reconstructed exclusively using at least one part of the m ultrasound time signals.

DE-A-10 2006 003 978 relates to a method for the non-destructive inspection of a test piece having at least one acoustically anisotropic material area using ultrasound. The direction-specific sound propagation properties describing the acoustically anisotropic material area are determined and provided. Also a coupling of ultrasound waves takes place in the acoustically anisotropic material area of the test piece and a reception of ultrasound waves reflected in the interior of the test piece with a plurality of ultrasonic transducers.

The ultrasound signals generated by means of the plurality of ultrasonic transducers are evaluated such that the evaluation takes place in a direction-selective manner using the direction-specific sound propagation properties.

In the case of the method, a test piece is employed with n ultrasonic transducers, of which a number i ultrasonic transmitters is established, which are activated at the same time. Via the number i of the ultrasonic transmitters and the concrete assembly of the transmitter group, in particular its arrangement on the surface of the test piece, the entire radiation characteristic (aperture) of the transmitter group and in addition the sensitivity and the resolution power of the measurements is determined. Certainly, the number i is smaller than the total number of the ultrasound transmitters of the test piece. The total radiation characteristic is determined exclusively via the number i of the ultrasonic transmitters.

U.S. Pat. No. 4,989,143 relates to a coherent energy beam display and in particular to a new method for the improved adaptive formation of a coherent beam using interactive phase conjugating, in order to counteract effects of the inhomogeneous wave deflection. Details for the improvement of the signal energy and readout for phased array-applications for different defect depths cannot be learned from this publication.

A further method is described in EP-B-1 649 301. In the case of this method, a complete wavefront is emitted onto at least one test section of the object using a plurality of independent emission elements.

Subsequently, a wave reflected by the structure of the object is received by means of a plurality of receiver elements independent of one another. The signals received from the receiver elements are digitalized in digitalizing steps and processed further. A dynamic depth focusing or an aperture adaption is not raised in EP-B-1 649 301.

In U.S. Pat. No. 7,263,888 a two dimensional phased array for the volumetric ultrasound testing as well as a method for the use of the phased array is described. The phased array consists of a plurality of ultrasound oscillators, which are arranged in a right-angled design. The two-dimensional array permits the electronic adjustment of combustion point properties and of the dimensions of the aperture/orifice both in lateral as well as in height directions, so that uniform and/or specified sound-field characteristics can be attained at any or all positions in the tested components.

A modulation can be applied to each of the ultrasonic elements, in order to form a sample beam and to scan at least one area of the test material with the sample beam.

Compared to a 1-dimensional linear array, the 2-dimensional phased array offers the advantage that this is separated and/or divided in a plurality of discrete ultrasound oscillators, which extend both in the X as well as in the Z-direction. As a result, the formation of a sample beam can occur both in the X-Y plane as well as in the Z-Y plane. This permits a 3-dimensional steering/control of the sample beam with regard to the focal distance depth, steering angle and focal distance geometry. The steering of the aperture also contributes to the formation of the sample beam. The aperture of the array can be selected by multiplexing the sample beam by connecting synchronous channels with individual ultrasonic oscillators of the array. Also, the dimensions of the aperture can be controlled and/or adjusted both in the X as well as in the Z direction.

A method and a device for the ultrasonic testing of different zones of a workpiece are described in U.S. Pat. No. 5,533,401. A plurality of ultrasound transducers with focus zones with different sized depths is thereby arranged, in order to test a bar-shaped titanium-body with regard to its thickness. The focus zones partially overlap the adjacent focus zones, so that a complete inspection of the thickness of the entire bar section is ensured. The reflected signals of the transducer-receiver are processed in digital form, in order to generate an image of the bar-section.

Such a method, however, is expensive, since each probe must be adjusted individually and an adjustment of the surface unevenness is difficult.

SUMMARY OF THE INVENTION

Consequently, the task of the present invention is to further develop a method and a device of the type mentioned at the outset, to the effect that the signal energy and resolution is improved for phased array-applications for different defect depths.

The task, according to the present invention, is solved among other things by the characteristics of claim 1. Through the invention it is achieved, that already during reception, a continuous modification of delay values and/or the number of receiver elements occurs for each digitalizing step. An improvement of the sound energy and the resolution for phased array-applications is achieved for different defect depths "on-the-fly" with a receiver/transmit clocking with a continuous focal law, i.e., modification of the delay values and number of transmit/receive elements or optionally by combination of different focal laws.

The continuous modification of delay values and/or number of transmit/receiver elements for a virtual probe occur during the reception of the HF-signals by a suitable firmware-program "on-the-fly."

Overall, higher performance and improved error detection is achieved with reduced testing costs compared to the prior art.

Through the method according to the present invention, a dynamic depth focusing (run-time controlled focusing) and dynamic aperture-adaption (run-time controlled receiving aperture) of the receiving part of a phased-array application are carried out. The focal law or the delay values and the number of transmit/receiver elements of the virtual probe are changed next by a digitalization step.

According to a preferred procedural method the delay values of a stored start delay (focal law for the surface position) up to an end delay (focal law for the rear wall position) are calculated by means of a distance function 1/R with R=radius.

Optionally, the delay values can be stored in a reference table, particularly in the case of complex coherence.

A further procedural method is characterized by the fact that an aperture-adaption occurs through linear modification of the start elements of the virtual probe to the number of the end elements.

The start of the aperture-change can be triggered with the "time-of-flight"-position of the surface-interface-echo.

A further method step is characterized by the fact that the summation of different focused transmitter-shots at a signal occurs through use of a digital TGC-function. It is thereby provided, that the sensitivity difference occurring in the assembly of transmitter-shots focused in different depths at a signal during the zone transition are balanced out by use of a digital TGC-function.

According to an independent inventive concept, the invention additionally relates to a method and a device for the definition of time delays for phased array probes through functional dependencies, such as for example by means of a BEZIER-function, a polynomial or other type of function. The function uses the indices of the ultrasonic transducer element as a criterion and displays the delay as result, while the parameters are set depending on the application.

A further property of the invention consists in that all of the above-mentioned methods according to the present invention can be combined in any form with each other or carried out in succession.

Moreover, it is the subject matter of the invention, that the digitalized signals received by the ultrasonic transducers are stored in a suitable electronic device. For the expansion of the evaluation, for example in the above-mentioned form, the stored data can then be consulted.

In the case of the prior art, the problem is that the number of applicable delay-sets for the arrangements is ultimately limited by the capacity of the hardware and processing times for the data transfer. With a greater number of elements and additional zones, which are to be tested, the demand for storage space increases.

In addition, the zone for varying delay laws requires special treatment, so that no discontinuity occurs within the images produced by the ultrasound device. In order to resolve this, modern instruments calculate the delay based on a distance-algorithm for very small zones or for each scanned point. This distance-algorithm is only suited for sufficiently homogeneous media without strong discontinuities, as these are common in the case of non-destructive testing. During the distance calculation, fixed relationships were already utilized, in which, however, a significantly higher number of parameters was required.

According to the inventive concepts of one's own described here, this problem is solved through the use of functional descriptions for the delay-generating switching circuits. The delays, which are generally used for ultrasound problems, can be defined by a static and differential function between the first element of the arrangement and the last element of the arrangement. The functional descriptions permit the generation of a curve for the delays of all elements, in which the delay value is a function of the arrangement number. For a 1-dimensional arrangement, this is a function with one variable, for 2-dimensional arrangements, it is a function of at least two variables, etc.

The functional description contains, in addition, a limited number of parameters. These parameters change for each of the selected delay zones and are to be adjusted individually.

A 1-dimensional virtual probe with 32 transmitter/receiver elements, for example, requires 64 delay values for a second zone. If a functional description is used in the form of a cubic BEZIER-function, the number of required parameters for a second zone can be reduced to 8 values: 4 values for emission and four values for receiving.

In order to even the transition between the delay zones, linear interpolations can be made between the functionally described values of two zones depending on the time difference between the currently viewed scan and two reference-time positions. The same formula can be used for the apodization or the overlap weighting. Here the result of the functional description is the amplitude for the element of the arrangement. The criterion is the element itself and the parameters are transferred within the ultrasound system or calculated in advance for higher-dimensional cases and filed in a table for the transfer.

Through the solution according to the present invention, the advantages are achieved compared to the prior art, that considerably fewer parameters are to be transferred, so that less storage space is required. Also the number of cycles can be augmented and an adaption to highly complex geometrical situations is also possible.

In summary, the method according to the present invention is characterized in that parameterizable functions for the delay-zones are employed instead of fixed formulas or delay-sets.

According to a further inventive concept of one's own the invention relates to a use of a 2-dimensional phased array probe and a probe mount for the testing of plate-like material such as thin or thick sheet metal. For this a 2-dimensional phased array is employed using dynamic depth focusing and dynamic depth aperture for improvement of the signal quality.

In the prior art dual, contact probes are used with water-film coupling and plastic-interface. Each of up to 100 probes must be set down individually, which requires a high expense for control technology. In addition, the probes must be inspected regularly for suitable ultrasonic coupling quality.

Since each probe can only be operated, when the latter is completely covered by the plate to be tested, plate edges have a non-inspected maximum zone, which is as wide as the width of the individual probe. This width is at present in the range of 50 mm.

The task of the further inventive conceptions is to further develop a device for the testing of two-dimensional material such as thin or thick sheet metal, such that a uniform sensitivity is achieved regarding a wide range of thickness. Also, the device should be improved to the effect that no mobile parts are required and this is applicable, without additional equipment to test the two-dimensional materials close to the edge. A novel and inventive use of a phased array is suggested.

To solve the task it is provided, that a 2-dimensional phased array probe is employed using dynamic depth focusing and dynamic aperture adjustment for the improvement of the signal quality and resolution. The mechanical design of the probe and probe mount is simplified by an ultrasound coupling via segment immersion technique.

Through replacement of matrix-array scanning units, which are individually programmable to individual thickness zones, the poor resolution of conventional immersion technique scanning units can be overcome.

In contrast to the conventional water-gap technique, the immersion technique permits a much simpler mechanical solution and requires no additional scanning units tracking the edges, in order to permit an inspection close to the plate edges.

Compared to the prior art, a greater mechanical simplification and higher resolution of defects are achieved. In addition, the on-site immersion technique is less sensitive to unevenness on the surface of the material to be tested.

The method and the device are suitable for testing thin or thick sheet metal in the thickness range of 4 to 400 mm.

The pixelization over a plate width is conventionally between 12 and 17 mm, whereas 4 to 8 mm can be achieved with the technology according to the present invention.

BRIEF DESCRIPTION OF THE DRAWINGS

Further particulars, advantages and characteristics of the invention arise not only from the claims, the characteristics to be drawn from these—in themselves and/or in combination—, but also from the preferred execution examples to be drawn from the description of the drawings.

FIG. 2*a*)-*d*) shows a diagram of a top view of a probe in the transmit/receive state, FIG. 3 shows a diagram of a probe with different test clockings, FIG. 4*a*), *b*) shows a diagram of a probe above a non-ideal switch-on geometry as well as an illustration of a parallel B-scan, FIG. 8 shows a diagram of a probe with different test clockings, FIG. 9*a*), *b*) shows a lateral view of a probe bar as well as the top view of a probe bar.

DETAILED DESCRIPTION OF THE INVENTION

Figure 1:
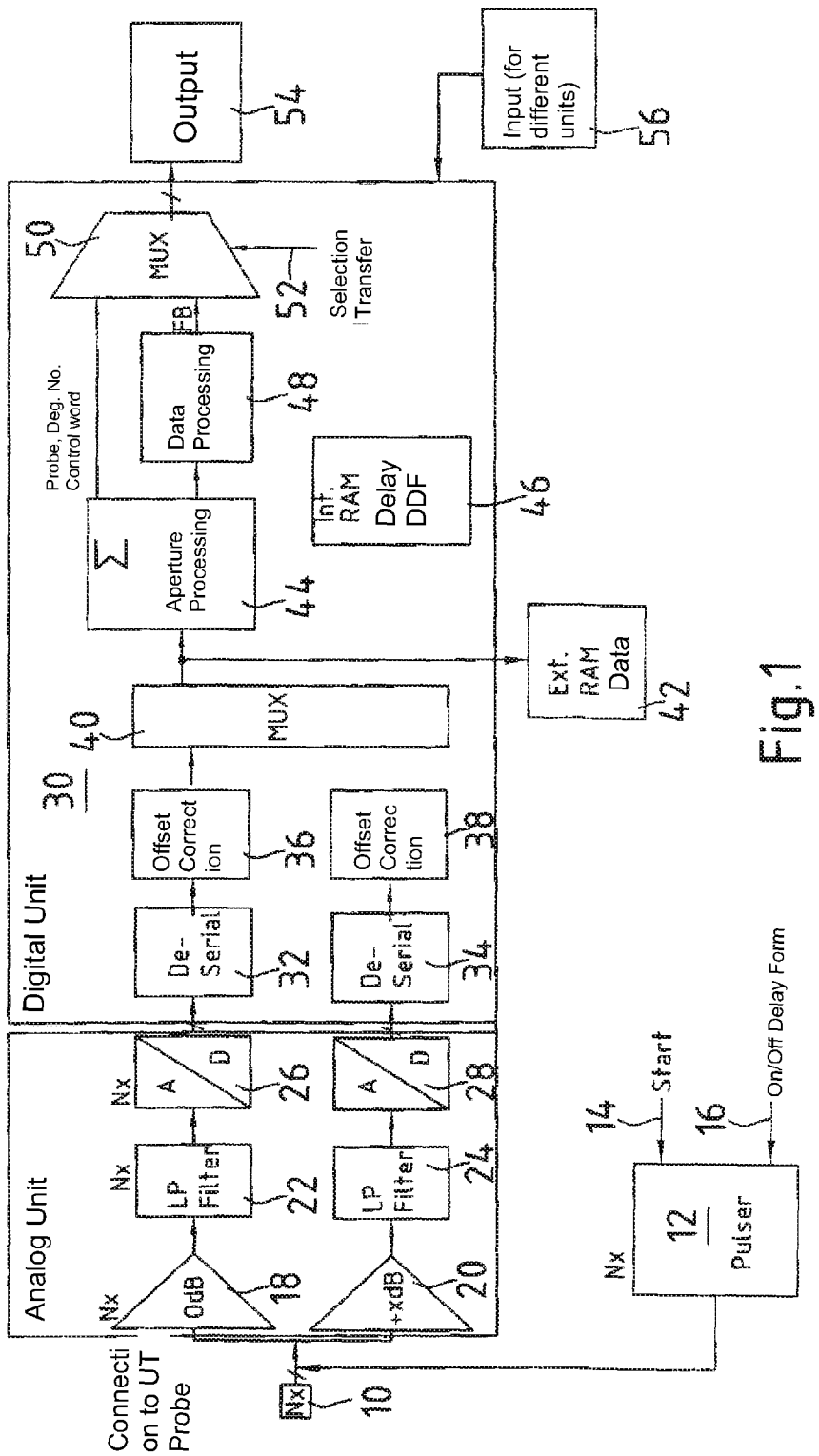
FIG. 1 shows a block diagram of a control unit for phased array probes.

FIG. 1 shows a block diagram of a control unit comprising preferably N=128 channels. For each of the up to N=128 ultrasonic transducer elements 10, a pulser 12 is provided, which is controllable via an input 14. A delay time, for example, of 5 ns can be switched on or off via a further input 16. The signals received by the ultrasonic transducer elements 10 are collected on two channels, in which each channel includes an operational amplifier 18, 20, a low-pass filter 22, 24 as well as an A/D-transducer 26, 28. The operational amplifiers 18, 20 of the individual channels have different amplification. The A/D-transducers are connected to their digital outlet, i.e., with a programmable integrated switching circuit 30. The digital outlet of the A/D-transducer 26, 28 is connected to an input of a De-Serial-device 32, 34. An outlet of the De-Serial-device is connected to the input of an offset-correction-device 36, 38, whose outlets are connected to a multiplexer 40. The multiplexer 40 is connected on the outlet side to an external memory element 42 such as RAM and to a processing unit 44.

In the processing unit 44, a channel selection and also a depth focusing as well as a dynamic aperture-adjustment occur. By way of example, 5 ns is provided as delay time. An output of the external memory element 42 is connected to the aperture-processing unit 44. Also, an internal memory element 46 is provided, which is also connected to the aperture-processing unit 44.

An outlet of the unit 44 having a summing member is connected to a processor 48, in which the amplification, filtering, time-control amplification a real-time HF-amplitude scaling is carried out in a digital manner.

A signal is transferred to the outlet of the processor 48, which is connected to a first input 52.1 of a multiplexer 50. A header, a sequence number or a control word can be connected to a second input 52.2 of the multiplexer. The respective input can be selected via a third input 52.3. For example, a 17 bit signal abuts the outlet of the multiplexer 50, which is made available via a fast serial link 54 for further processing. A further component of the switching mechanism is an input-device 56 for the input of signals to different units of the switching circuit 30.

The method according to the present invention is carried out as follows. First, a complete wavefront is emitted via the pulser 12 through simultaneous (phase-fixed) control of all ultrasonic transducer elements perpendicular to at least one section of the object to be tested. Subsequently, a wave reflected by the structure of the object is received by means of a plurality of ultrasonic transducer elements 10 independent of one another. The signals received by the ultrasonic transducer elements 10 are digitalized in a digital signal processing unit in digitalization steps, processed electronically and stored in the memory element 42 or 46.

At the same time, a continuous change of delay values and/or the number of ultrasonic transducer elements of a virtual probe takes place for each digitalization step on-the-fly, since for each digitalization step on-the-fly the delay values and/or number of ultrasonic transducer elements are adjusted. The delay values are calculated from a stored start delay (focal law for the surface position) up to an end delay (focal law for a real wall position) by means of a distance function such as, by way of example, 1/R with R=radius. The delay values can be stored in a reference table, particularly in the case of complex coherence. In the present case, the delay values are filed in the form of a curve.

The aperture-adaption is effected through linear modification of the number of receive elements, preferably in the summing member 44.

Usually a strong change in the delay values and/or aperture-adaption is triggered by the "time-of-flight"-position (run-time position) of the surface-interface-echo. In the summing device 44, a summation occurs of differently focused transmitter-shots on a signal by using a digital TGC-function. In addition, the delay values can be defined by functional dependencies by means for example of a BEZIER-function, polynomial or other type of function, in which the function indices of the ultrasonic transducer elements are used as criterion and the delay values are displayed as a result, while parameters are set depending on the application.

In the FIGS. 2a to 2d, purely diagrammatic top views of a probe 62 are depicted in the form of a matrix-phased-array probe. The latter consists of a plurality of individual ultrasonic transducer elements 10, which are individually controllable.

As already previously explained, all ultrasonic transducer elements 10 are activated simultaneously for sending, as is depicted in FIG. 2a.

In FIGS. 2b to 2d for focal zones to be interested in, according to the principle of run-time controlled focusing (dynamic depth focusing) as well as run-time receive-aperture (dynamic aperture), one element, as in FIG. 2b, five elements, as in FIG. 2c, or nine elements as in FIG. 2d, are switched to receive, in order to focus on zones of different depths.

Each probe 62, by way of example, can have 128 ultrasonic transducer elements 10. Preferably, probes are employed with 5×25=125 elements, whereby an active surface, for example, is achieved in the range of 35 mm×175 mm.

In order to cover sheet widths in the range of 1000 mm to 5300 mm, approx. 36 probes 62 are required.

A system probe 64 with 24 elements is depicted in FIG. 3, in which according to the system test clocking T1 . . . Tn in each case nine ultrasonic transducer elements 10 are gradually switched on and are switched to receive.

Through the method according to the present invention compared to the conventional attachment technique a greater coupling reliability is achieved in the case of rough surfaces. Also all probes can be arranged without a gap over the entire sheet metal width, in the case of a width pixelization, for example, of 6 mm. Edge and top/bottom testing are integrated into the concept. Also, more significant reconstruction methods can be incorporated through early digitalization of all test data. Also, the parallel-B-scan principle is permitted, i.e., transmitting and receiving all ultrasonic transducer elements simultaneously.

Through the parallel-B-scan-method, robust testing is also permitted in non-ideal switch-on geometries 66, as depicted in FIG. 4a. The non-ideal switch-on geometry 66 can, for example, have a curved front wall and/or curved rear wall, as depicted in FIG. 4b.

Figure 5:
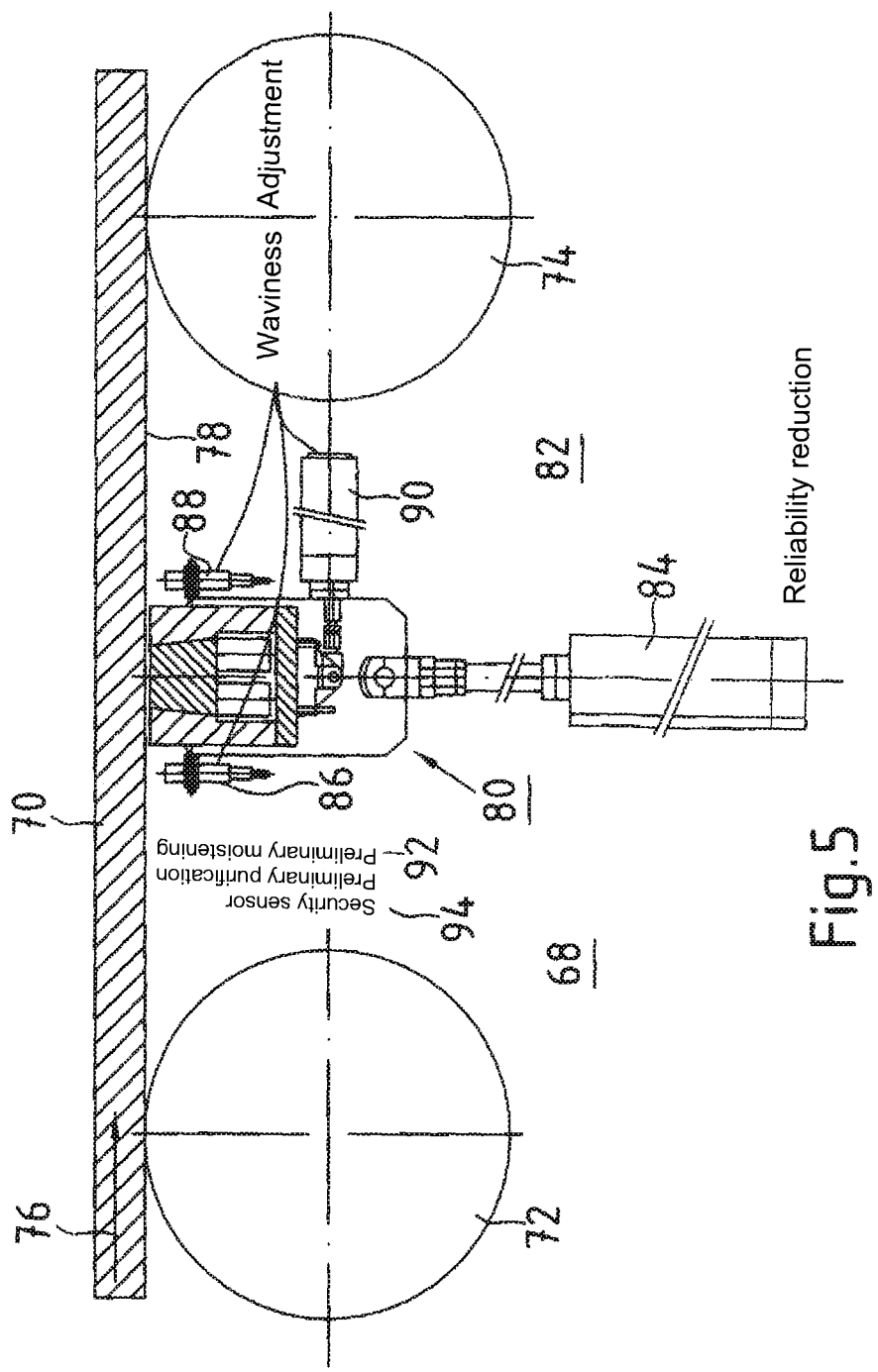
FIG. 5 shows a diagram of a first embodiment of a probe arrangement in local immersion for the testing of a two-dimensional material from the bottom

A first embodiment of a test arrangement 68 is depicted in FIG. 5 in lateral view. An object 70 to be tested in the form of a two-dimensional material such as thin sheet metal or thick sheet metal is stored on rollers 72, 74 and is transportable in the direction of the arrow 76. On a rear side 78 of the material 70 to be tested, a probe arrangement 80 is provided, by means of which the individual probes PK1-PKn are coupled via a segment technique to the material 70 to be tested. The probe arrangement 80 is designed as a water chamber opened upwards, which via a constant coolant inlet counterbalances the water loss, which arises in the crack of the object 70 to be tested and thus guarantees a flawless coupling of the ultrasound. The probe arrangement 80 is preferably sealed with a lip-seal on the rear side of the material to be tested, in order to reduce the water loss. Alternatively, start-up and outlet sliding blocks can also be provided in the direction of movement 76 of the device under test 70, in order to protect the probe arrangement 80 against damage in the case of too great unevenness of the device under test. The probe arrangement 80 can be lowered via an actuator 84 and dynamically readjusted with further actuators 86, 88, 90 for waviness adjustment. A preliminary purification or preliminary wetting 92 as well as a security sensor 94, which in the case of failure arranges a cut-off, is upstream of the probe arrangement 80.

Figure 6:
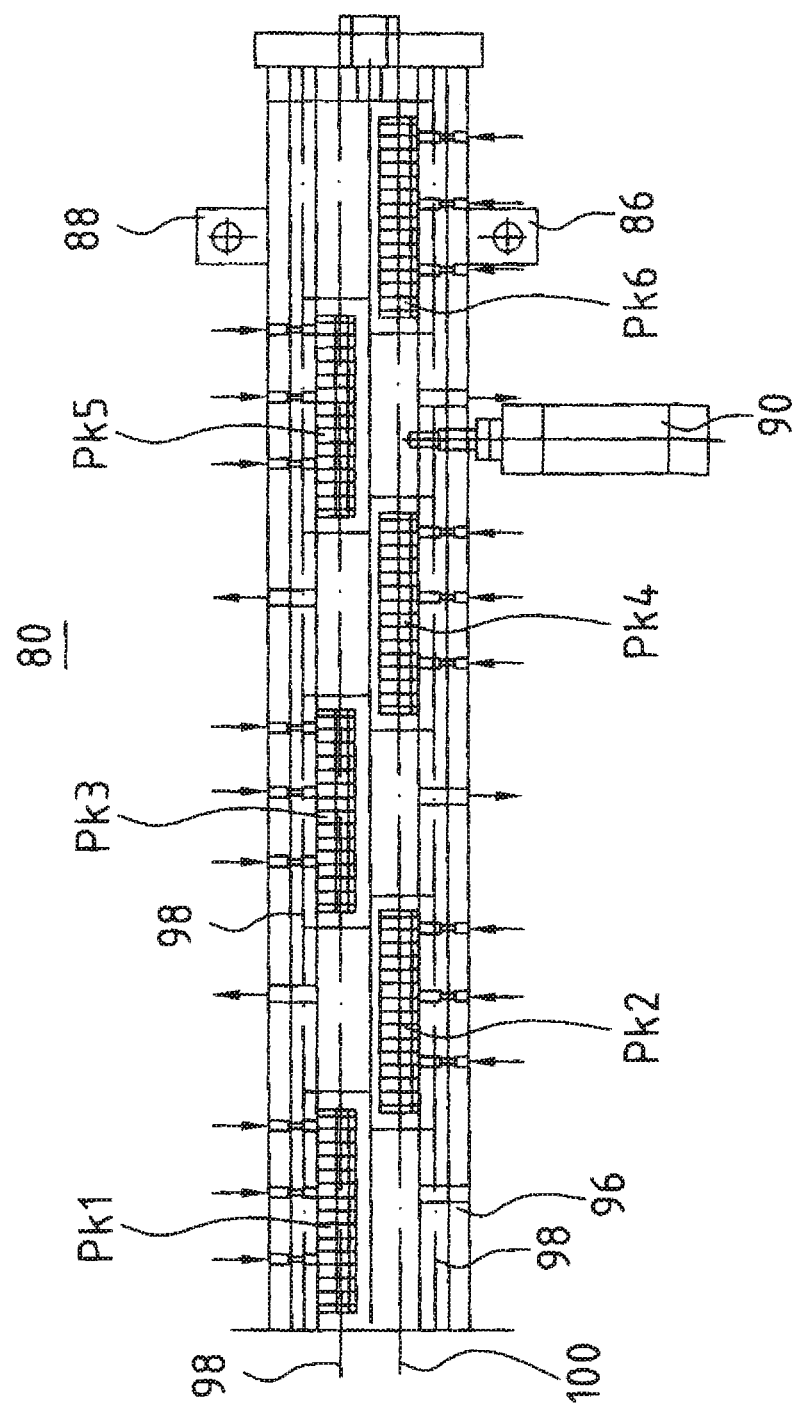
FIG. 6 shows a top view of the probe arrangement according to FIG. 5, FIG. 7*a*)-*d*) shows a diagram of a top view of a probe in the transmit and receive state.

FIG. 6 shows a top view of the probe arrangement 80, in which individual probes PK1-PK6 or PKn are arranged within a water basin 96. The water basin is covered by means of a preferably circumferential sealing element 98 such as lip seal for the rear side 78 of the material 70 to be tested. Thereby, the probes PK1, PK3, PK5 are arranged along a first longitudinal axis 98 at a distance from each other, in which the probes PK2, PK4, PK6 are arranged along a second axis 100 running parallel to the first axis such that these run offset to the probes PK1, PK3, PK5. In this manner, an overall width B of the area to be inspected is covered by ultrasonic transducer elements. Each of the ultrasound probes Pk i is connected here to one of the ultrasound control units i (according to FIG. 1). In this manner, the testing can be carried out simultaneously parallel to each individual probe and thus the test performance can be increased. Within a probe depending on the test requirement a group of preferably 5×5 elements of the matrix probe is emitted focused on the rear wall of the device under test. The evaluation of the same receive group then occurs depending on the depth zone via the described dynamic aperture adjustment through the selection of the corresponding receive elements and/or a dynamic depth focusing via the adjustment of the delay times. In order to cover the entire probe area, the described group continues to be clocked in the next ultrasound shot, a matrix element, until the entire probe aperture was scanned. Alternatively, in a further test mode the transmit side aperture (for example, only the center element or a 3×3 element group) can be activated with appropriate focusing and the stored received ultrasonic signal from the different transmit shots assembled according to the depth zone can be reevaluated with aperture and focusing adjustment. A further test mode exists in a transmit shot of the entire aperture of the probe (for example, 5×25 matrix elements) with a linear focusing on the rear wall of the device under test and an evaluation of the stored receive signals corresponding to the method described at the outset of the through-clocking of a 5×5 element group.

The probe arrangement 80 is able to carry out a test of 100% of the area of untrimmed rolled plates in the process of manufacture. Thereby, test sheet metal dimensions with lengths up to 30,000 mm, widths of 1000 to 5300 mm and thicknesses in the range of 4 mm to 300 mm can be treated and inspected.

The testing can take place in a flow, in particular surface and edge zone testing, in which these can take place longitudinally and transversely. The test speed is approx. 0.5 m/sec at 1000 ultrasound-shots/sec.

The coupling occurs—as explained above—via water gaps per cycle of water supply.

The method according to the present invention permits a reliable detection depending on the material thickness, in which in the case of a thickness of 8 mm to 240 mm ERG Ø3 up to a distance of 3 mm to the surfaces and in a thickness range of 240 mm to 400 mm ERG Ø5 up to a distance of 5 mm to the surfaces are reliably detected.

Overall, a modular design is aimed at in order to increase functional reliability, availability and maintainability.

The method can be verified for example under the following conditions.

Testing method: Pulse echo—method in the case of a water distance of 80 mm

Probe 1:
Material: carbon steel
Dimensions: length=200 mm, width=100 mm
Thickness: 280 mm
Test defects: shallow saddle holes, diameter 3 or 5 mm
Probe 2:
Material: carbon steel
Dimensions: length=100 mm, width=100 mm
Thickness: 20 mm
Test defects: blind hole, diameter 3 or 5 mm
Transducer (Probe 1):
Type: 2D-Face Array Transducer (18 elements)
Frequency: 4 MHz
Element dimensions: 7×7 mm$^2$
Transducer (Probe 2):
Type: 2D-Face Array Transducer (24 elements)
Frequency: 5 MHz
Element dimensions: 6×6 mm$^2$ The diagram of a matrix-probe is depicted in FIG. 7. According to FIG. 7a, the probe PK includes 5×5=25 individual transmit/receive elements 10. The principle of the runtime controlled focusing (dynamic deep focusing) of the runtime controlled receive aperture (dynamic aperture) is to be learned from FIGS. 7b) to 7d). According to the evaluation of the number of received ultrasound signals of probe PK, different zones (Zone 1, Zone 2, Zone 3) of a test object can be inspected, as purely schematically depicted in FIG. 7e).

FIG. 8 shows, for example, a gapless sequence of individual probes PK1 . . . PKn for a system probe APK or a probe bar PKL, which in turn arises through a gapless sequence of system probes APK.

After the emission of the wavefront by all probes PK1 . . . PKn all ultrasound receivers 10 of the probes PK1.

PKn are switched to receive, so that the incoming ultrasound signals can be digitalized in digitalization steps and can be stored. Based on the temporally incoming digitalization, in which the signals are digitalized at any point in time, the signals receive depth information, which can be evaluated. In a first test clocking T1, the 25 individual signals of each probe PK1 . . . PKn are evaluated "on-the-fly," i.e., during the reception of the signals. In the further test clockings T2 . . . T5 an evaluation takes place of already stored ultrasound signals, as they continue to be clocked in a "virtual probe," considering a continuous change of the delay values and/or the number of receive elements for each digitalization step. Based on the digitalization, each stored value also receives depth information, which can be evaluated. In the execution example depicted with probes PK with 25 transmit/receive elements, an evaluation can thus be made within 5 test clockings.

An individual probe PK1 . . . PKn thereby consists, for example, of 5×5=25 individual transmit/receive elements 10 with dimensions in each case, for example, of 6×6 mm. Thus, dimensions result for a probe housing PKG depicted in FIG. 9a in the range of approx. 35 mm×34 8 mm with 25 transmit/receive elements. A probe bar PKL is depicted in FIG. 9b.

In the case of a sheet metal width, for example, of maximally 5350 mm and an assumed probe housing width in the case of 25 transmit/receive elements of 35 mm a required probe number results of 5350/35=153 for covering the sheet metal width.

Assuming that for each control unit SE 125 channels are available, a probe number results of 5 per electronic unit. For a required probe number of 153, 31 electronic units are necessary.

Using 31 electronic units, which can each process 5 probes, a maximum probe number results of 155, from which it results, that a width coverage of 155×35 mm=5425 mm is possible. This corresponds in the case of a sheet metal width of 5350 mm to an overlap of 75 mm.

Figure 10:
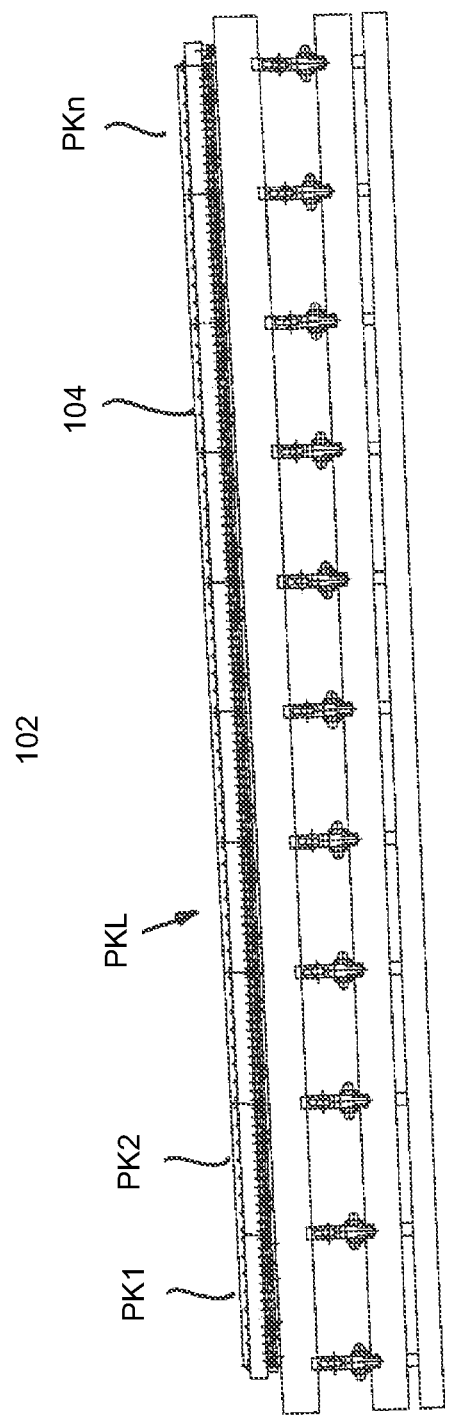
FIG. 10 shows a front view of a second embodiment of a probe-arrangement in the form of a probe bar.

FIG. 10 shows a front view of a second embodiment of a test arrangement 102 in the form of a probe bar. With this arrangement, the probes PK1 . . . PKn are placed in a gapless row according to FIG. 9 as probe bar PK1, in order to permit the complete testing of a two-dimensional material such as, for example, a sheet metal 104.

Figure 11:
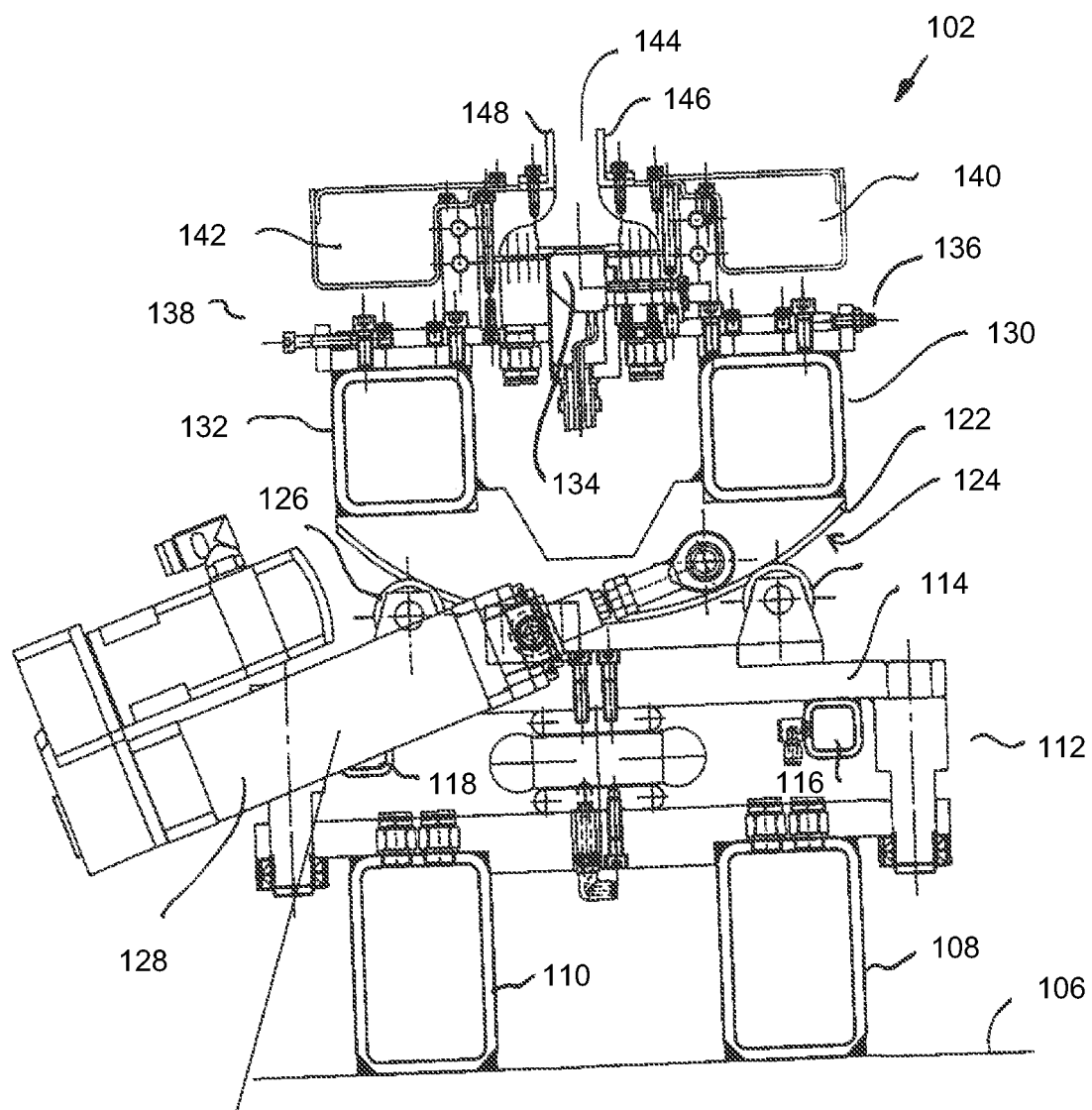
FIG. 11 shows a lateral view of the probe bar according to FIG. 7

A lateral view of a first embodiment of the probe bar 102 is depicted in FIG. 11. The probe bar 102 is arranged on a stationary or mobile support 106, which is not described in detail.

On this support, carriers 108, 110 run, which are designed for water intake. On the carriers 108, 110 a lifting device 112 is provided, by means of which the probe bar 102 can be moved towards the sheet metal 104 to be tested. The lift device can be designed pneumatically and can have a range of approximately 20 m in the extended state. The lift device 112 includes a height-adjustable platform 114, under which channels 116, 118 are arranged for the air supply.

In the preferred embodiment, the probe bar 102 is designed with an angle adjustment device 120, including a curved tray 122, which are pivot mounted on rollers 124, 126 and is adjustable via an adjustment mechanism 128. The angle can be adjusted in the range of +/−5°.

The tray is provided with carriers 130, 132 running longitudinally, by which the probe bar 134 is carried securely. For the arrangement of the probe bar 134, particularly in the case of the initial assembly, adjustment elements 136, 138 are provided, which are supported on an upper surface of the carrier 130, 132, On the side of the probe bar 134, collecting channels 140, 142 are arranged for draining or stripping of coupling water. Above the probe bar a groove 144 is provided for the coupling of the water to the material to be tested, which is limited laterally by rubber diaphragms 146, 158, which abut on a rear side of the material to be tested.

Figure 12:
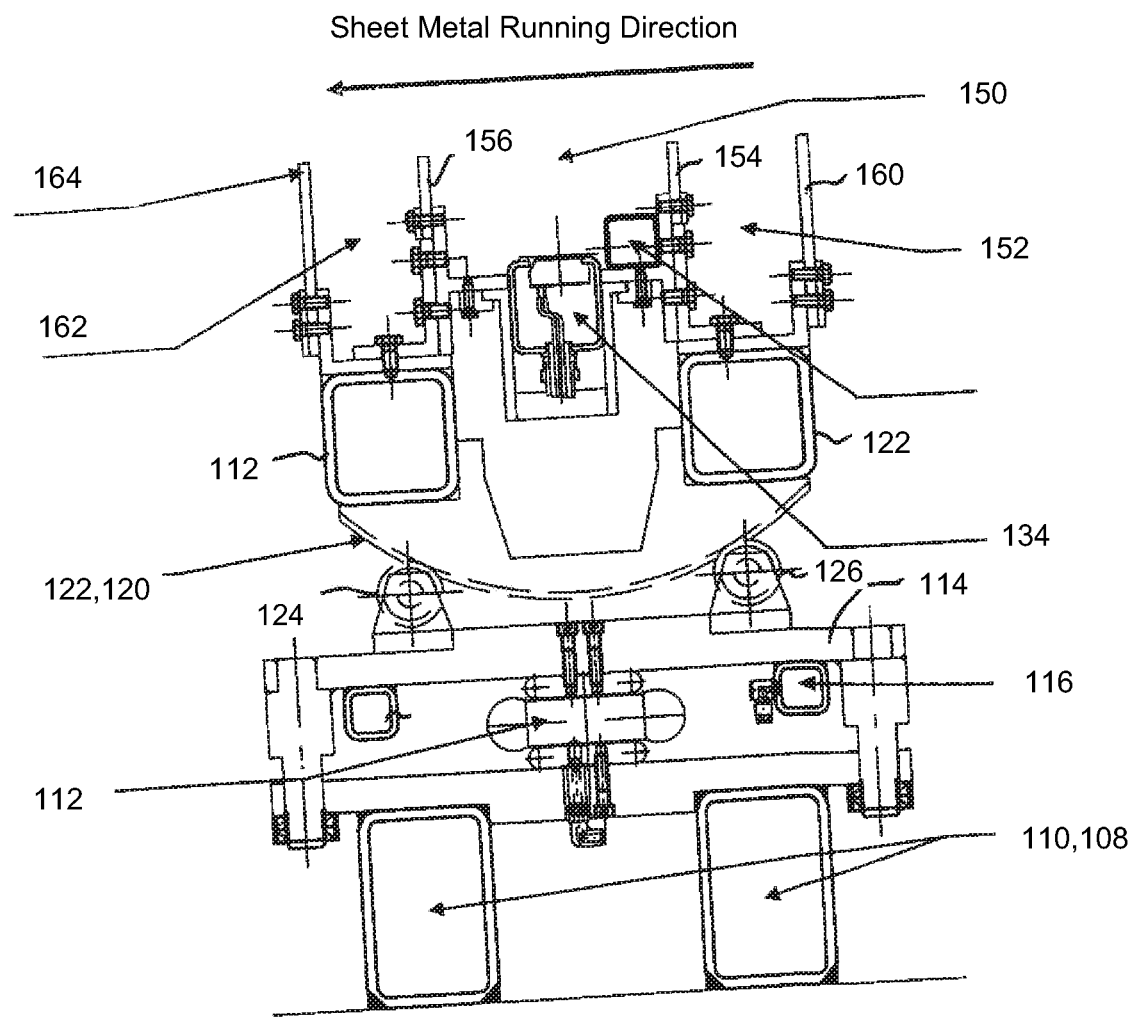
FIG. 12 shows a lateral view of a further embodiment of a probe bar.

FIG. 12 shows a further embodiment of a probe bar 150 in lateral view, which corresponds significantly to the embodiment according to FIG. 11, so that the same elements are identified with the same reference numerals.

In the case of this embodiment, the probe bar 134 leads to a test tray 152, which is limited laterally by stripping and sealing lips 154, 156. Parallel to the test tray, a preliminary moistening-channel 158 is provided in the direction contrary to the running direction of the sheet metal, by means of which the material to be tested is moistened. The channel is limited laterally by a stripping and sealing lip 160 as well as by the stripping and sealing lip 154.

In the running direction of the sheet metal, a collecting channel 162 runs parallel to the test tray 152, in which water emerging from the test tray is received. The collecting channel is limited laterally by a stripping and sealing lip 64 as well as the stripping and sealing lip 156.

The invention claimed is:

1. A method for processing signals, which are generated by the reflection of ultrasonic waves by defects of the structure of an object during the non-destructive testing of objects the method comprising:
    emitting a complete wavefront onto at least one test section of the object using a plurality of independent emission elements,
    receiving a wave reflected by the structure of the object by means of a plurality of receiver elements that are independent of one another, where the plurality of receiver elements is arranged in a 2-dimensional phased array,
    digitizing the signals received by the receiver elements in digitalization steps, and continuously modifying one of delay values and the number of receiver elements for each digitalization step.

2. Method according to claim 1, wherein the delay values of a stored start delay up to an end delay are calculated by means of a distance function 1/R with R=radius.

3. Method according to claim 1, wherein the delay values are stored in a reference table.

4. Method according to claim 1, wherein an aperture-adaption is effected b linear modification of the number of receiver elements.

5. Method according to claim 1, wherein one of a start of the modification of the delay values and aperture-adaption is triggered by the "time-of-flight" position of the surface-interface-echo.

6. Method according to claim 1, wherein a summation of different focused transmitter-shots for one signal is effected by application of a digital TGC-function.

7. Method according to claim 1, wherein delay values are defined by functional dependencies in which the function uses element-indices as criterion and displays the delay values as a result, while parameters are set depending on the application.

8. Method according to claim 1 wherein delay values are generated by one of a linear combination of one or several instances of a generating method and by linear combination of different instances of several generating methods mentioned.

9. Method according to claim 1, wherein the data are buffered on an electronic memory element and then are processed.

10. A method for processing signals, which are generated by the reflection of ultrasonic waves by defects of a structure of an object during non-destructive testing of objects the method comprising:
   emitting a complete wavefront onto at least one test section of the object using, a plurality of independent emission elements,
   receiving a wave reflected by the structure of the object by means of a plurality of receiver elements that are independent of one another, where the plurality of receiver elements is arranged in a 2-dimensional phased array,
   digitizing the signals received by the receiver elements in digitalization steps, and
   continuously modifying delay values of receiver elements for each digitalization step.

11. Method according to claim 10, wherein an aperture-adaption is effected by linear modification of a number of receiver elements that are switched to receive.

12. Method according to claim 10, wherein a start of the modification of the delay values is triggered by a "time-of-flight" position of a surface-interface-echo.

13. Method according to claim 10, wherein a summation of different focused transmitter-shots for one signal is effected by application of a digital TGC-function.

14. Method according to claim 10, wherein the delay values are defined by functional dependencies in which the function uses element-indices as criterion and displays the delay values as a result, while parameters are set depending on the application.

15. Method according to claim 10, wherein the delay values are generated by one of a linear combination of one or several instances of a generating method and by linear combination of different instances of several generating methods mentioned.

16. A method for processing signals, which are generated by reflection of ultrasonic waves by defects of a structure of an object during non-destructive testing of objects the method comprising:
   emitting a complete wavefront onto at least one test section of the object using a plurality of independent emission elements,
   receiving a wave reflected by the structure of the object by means of a plurality of receiver elements that are independent of one another, where the plurality of receiver elements is arranged in a 2-dimensional phased array,
   digitizing the signals received by the receiver elements in digitalization steps, and
   continuously modifying a number of receiver elements switched to receive for each digitalization step.

17. Method according to claim 16, wherein an aperture-adaption is effected by linear modification of the number of receiver elements switch to receive.

18. Method according to claim 17, wherein a start of the modification of the aperture-adaption is triggered by a "time-of-flight" position of a surface-interface-echo.

19. Method according to claim 16, wherein a summation of different focused transmitter-shots for one signal is effected by application of a digital TGC-function.

20. Method according to claim 16, wherein modifying the number of the receiver elements switched to receive is performed at least in part in order to focus on zones of different depths.

* * * * *

UNITED STATES PATENT AND TRADEMARK OFFICE
CERTIFICATE OF CORRECTION

PATENT NO. : 8,596,127 B2
APPLICATION NO. : 12/994471
DATED : December 3, 2013
INVENTOR(S) : Falter et al.

It is certified that error appears in the above-identified patent and that said Letters Patent is hereby corrected as shown below:

In the Drawings

In Fig. 2, Sheet 2 of 10, delete " aperture " and insert -- aperture --, therefor.

In the Specification

In Column 9, Line 54, delete "35 mm×34 8 mm" and insert -- 35 mm×34.8 mm --, therefor.

In Column 10, Line 32, delete "stripping of" and insert -- striping off --, therefor.

In Column 10, Line 52, delete "lip 64" and insert -- lip 164 --, therefor.

In the Claims

In Column 11, Line 9, in Claim 4, delete "effected b" and insert -- effected by --, therefor.

In Column 11, Line 23, in Claim 8, delete "claim 1" and insert -- claim 1, --, therefor.

In Column 11, Line 36, in Claim 10, delete "using," and insert -- using --, therefor.

Signed and Sealed this
Twentieth Day of May, 2014

Michelle K. Lee
*Deputy Director of the United States Patent and Trademark Office*